United States Patent
Sauvageau et al.

(10) Patent No.: US 7,655,006 B2
(45) Date of Patent: Feb. 2, 2010

(54) PERCUTANEOUS PRINGLE OCCLUSION METHOD AND DEVICE

(75) Inventors: David J. Sauvageau, Methuen, MA (US); Robert J. Garabedian, Tyngsboro, MA (US); Robert F. Rioux, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 761 days.

(21) Appl. No.: 11/207,628

(22) Filed: Aug. 18, 2005

(65) Prior Publication Data

US 2005/0288661 A1 Dec. 29, 2005

Related U.S. Application Data

(63) Continuation of application No. 10/232,763, filed on Aug. 30, 2002, now Pat. No. 6,962,588.

(60) Provisional application No. 60/316,738, filed on Aug. 31, 2001.

(51) Int. Cl.
*A61B 18/18* (2006.01)
*A61M 29/00* (2006.01)
(52) U.S. Cl. .................. 606/41; 607/101; 606/192
(58) Field of Classification Search ............ 606/41, 606/45–50, 191, 192, 194; 607/101, 102
See application file for complete search history.

(56) References Cited

U.S. PATENT DOCUMENTS

| | | | |
|---|---|---|---|
| 4,299,227 A | 11/1981 | Lincoff | |
| 4,332,254 A | 6/1982 | Lundquist | |
| 4,929,246 A | 5/1990 | Sinofsky | |
| 4,950,238 A | 8/1990 | Sullivan | |
| 4,976,711 A | 12/1990 | Parins et al. | |
| 5,507,744 A | 4/1996 | Tay et al. | |
| 5,709,224 A | 1/1998 | Behl et al. | |
| 5,800,378 A * | 9/1998 | Edwards et al. | 604/22 |

(Continued)

FOREIGN PATENT DOCUMENTS

JP 08-038611 2/1996

(Continued)

OTHER PUBLICATIONS

Japanese Office Action dated Oct. 30, 2008 for Japanese Patent Application No. 2003-524455, Applicant: Boston Scientific Limited (4 pages).

*Primary Examiner*—Michael Peffley
(74) *Attorney, Agent, or Firm*—Vista IP Law Group LLP (57) ABSTRACT

Methods and devices for occluding a vessel during a percutaneous ablation procedure. An elongated access device having a lumen and a tissue piercing, open distal end in communication with the lumen is used to percutaneously access a vessel that supplied blood to the tissue to be treated. An elongated balloon deployment device is used to deliver a balloon into the interior of the vessel. The balloon is inflated, resulting in the occlusion of the vessel. The tissue to be treated is ablated. Because there is little or no blood to transfer the thermal energy away from the heated tissue, the ablation procedure is performed more efficiently. The balloon may be subsequently deflated allowing normal flow through the vessel to return.

15 Claims, 5 Drawing Sheets

U.S. PATENT DOCUMENTS

| | | | |
|---|---|---|---|
| 5,807,395 A * | 9/1998 | Mulier et al. | 606/41 |
| 6,010,518 A | 1/2000 | Prywes | |
| 6,106,473 A | 8/2000 | Violante et al. | |
| 6,135,991 A | 10/2000 | Muni et al. | |
| 6,231,544 B1 | 5/2001 | Tsugita et al. | |
| 6,238,389 B1 * | 5/2001 | Paddock et al. | 606/41 |
| 6,423,056 B1 | 7/2002 | Ishikawa et al. | |
| 6,610,056 B2 * | 8/2003 | Durgin et al. | 606/41 |
| 6,692,494 B1 * | 2/2004 | Cooper et al. | 606/46 |
| 6,770,070 B1 * | 8/2004 | Balbierz | 606/41 |
| 7,306,591 B2 * | 12/2007 | Thomas et al. | 606/27 |
| 2001/0001114 A1 | 5/2001 | Tsugita et al. | |

FOREIGN PATENT DOCUMENTS

| | | |
|---|---|---|
| WO | WO 97/24074 | 7/1997 |
| WO | WO 00/06046 | 2/2000 |

\* cited by examiner

PERCUTANEOUS PRINGLE OCCLUSION METHOD AND DEVICE

RELATED APPLICATION DATA

This application is a continuation of U.S. application Ser. No. 10/232,763, filed on Aug. 30, 2002, now U.S. Pat. No. 6,962,588, which claims the benefit of U.S. provisional application Ser. No. 60/316,738, filed on Aug. 31, 2001, the disclosures of which are expressly incorporated herein by reference.

FIELD OF THE INVENTION

The present invention relates to methods and apparatus for performing tissue ablation and, in particular, to methods and apparatus for occluding vessels that supply blood to the tissue to enhance the effectiveness of the ablation.

BACKGROUND

Solid tissue tumors, such as those found in the liver, traditionally have been treated with systematic chemotherapy, surgical resection, or local radiation therapy. Many tumors, however, remain poorly responsive to these therapeutic modalities and necessitate the use of alternative treatments, such as thermal ablation of the tumor. Thermal sources for these treatment modalities include high-intensity ultrasound, laser, microwave, and radiofrequency (RF) energy. Of these different types of ablation techniques, RF ablation has proven to be safe, predictable, and inexpensive, and has emerged as the thermal ablation modality that most easily creates large volumes of tissue necrosis.

Although RF ablation of the tumor can be implemented during open surgery, it is most often performed percutaneously. One RF ablation technique utilizes a single needle electrode or a multiple needle electrode array that is inserted percutaneously using a surgical probe and guided with real-time ultrasound, computed tomography (CT) scan or magnetic resonance imaging (MRI) into the tumor. One properly positioned, the needle electrode is activated, and alternating current is transferred from the needle electrode into the surrounding tissue, causing ionic agitation of the surrounding cells, ultimately leading to the production of frictional heat. As tissue temperatures increase between 60-100° C., there is an instantaneous induction of irreversible cellular damage referred to as coagulation necrosis. The treatment area is monitored ultrasonographically for increased echogenicity during the procedure, which corresponds to the formation of tissue and water vapor microbubbles from the heated tissue and is used to roughly estimate the boundaries of the treatment sphere.

Often, when performing a RF ablation procedure, the presence of blood vessels within or near the tumor causes the conduction of thermal energy away from the target tissue and into the relatively cooler blood. This may cause irregular shaped ablation regions, or sometimes even prevent ablation. When such procedures are performed using open surgical procedures, a surgeon may typically clamp the respective blood vessel, e.g., by using his or her fingers or by using a pair of forceps, thereby reducing or eliminating the blood flow adjacent or through the ablation site. For example, if the tumor is within the liver, the portal vein and/or hepatic artery at the porta hepatis may be clamped. This technique is called a "Pringle maneuver."

When a percutaneous ablation procedure is performed, however, a Pringle maneuver may not be possible, due to the lack of direct access to the vessel and/or the distance from the abdominal wall to the vessel. Angiographic portal arterial, or major vessel balloon occlusion has been used to prevent or minimize blood flow through the ablation site. This technique, however, is not flexible in that the human vasculature often prevents or makes difficult the introduction of the balloon into certain blood vessels, e.g., the portal vein in the liver.

Accordingly, apparatus and methods for occluding vessels in connection with an organ being treated by an RF ablation or other hyperthermic procedures would be useful.

SUMMARY OF THE INVENTION

Aspects of the inventions are directed to methods and apparatus for occluding the blood flow through a vessel, e.g., a blood vessel, by inserting the distal end of a rigid elongated member into the vessel, and inflating a balloon associated with the elongated member to at least partially occlude the fluid flow through the vessel. This occlusion technique lends itself well to ablation procedures performed on tissue, such as, e.g., a tumor, with which the occluded blood vessel is associated, but can also be used in conjunction with other medical procedures.

In accordance with one aspect of the inventions, a method of occluding a vessel through which a fluid flows is provided. By way of non-limiting example, the vessel may be a blood vessel, such as, e.g., the hepatic artery or portal vein. The method comprises inserting a rigid elongated member, such as, e.g., a cannula or other type of percutaneously placed insertion tube or catheter, through a wall of the vessel, wherein a distal end of the elongated member is disposed within a lumen of the vessel. By way of non-limiting example, the rigid member can be percutaneously introduced into the vessel. Alternatively, the rigid member can be placed laparoscopically, endoscopically, or through a surgical incision.

The method further comprises expanding an occlusive device associated with the distal end of the rigid member, such that fluid flow in the vessel lumen is partially or completely obstructed. In a preferred embodiment, the occlusive device is an expandable balloon that is expanded by introducing medium into the balloon. The invention in its broadest aspects, however, should not be limited to a balloon as other expandable devices that have the capability to occlude the flow of fluid through a vessel in which they are intended to be disposed in can be used as the occlusive device. The occlusive device can be associated with the distal end of the elongated member in any of a variety of ways. By way of non-limiting example, the occlusive device can be mounted to the distal end of the elongated member, or can be introduced through the rigid member using, e.g., an elongated tubular member. The method can further comprise collapsing the occlusive device, such that fluid flow in the vessel is unobstructed.

In accordance with another aspect of the inventions, a method for performing an ablation procedure on tissue comprises performing the previously described method to partially or totally occlude the blood flow of a blood vessel associated with the tissue to be ablated. For the purposes of this specification, a blood vessel is associated with tissue if the blood flow through the blood vessel will either directly or indirectly adversely affect the ablation process if not occluded. For example, the blood vessel can supply blood to the tissue or away from the tissue and/or be adjacent to the tissue. The tissue can be, e.g., a tumor associated with a body organ, such as the liver. In this case, the blood vessel that is occluded can be the portal vein, or other major vessel.

The method further comprises ablating the tissue using, e.g., radiofrequency energy. Other types of ablation modalities are also contemplated, such as high-intensity ultrasound, laser, microwave. The method can further comprise collapsing the occlusive device, such that blood flow through the vessel is unobstructed. By way of non-limiting example, this can be accomplished intermittently throughout the ablation procedure and/or after the ablation procedure is completed.

In accordance with a third aspect of the inventions, a vessel occlusion assembly comprises a rigid elongated member having a tissue piercing distal end, and an expandable occlusive device configured to be expanded to partially or completely occlude fluid flow through the vessel when the distal end of the elongate member is disposed within a lumen of a vessel, e.g. a blood vessel or any other vessel that transports fluid. The occlusive device can also be collapsible so that it can be collapsed to allow fluid flow through the vessel. The occlusive device can be, e.g., a balloon configured to be expanded when a medium is introduced into the balloon. If collapsible, the balloon can be deflated by removing the medium from it.

The occlusive device can be variously associated with the distal of the rigid member. For example, the occlusive device can be mounted to the distal end of the elongated member. Or the elongated member can include a device introduction lumen, in which case, the occlusive device can mounted to the distal end of another elongated member that is slidably disposed within the device introduction lumen. The distal end of the rigid member can have a sharpened tip, so that the rigid member can be percutaneously introduced into the vessel. The vessel occlusion assembly may further comprise a handle mounted to the proximal end of the rigid member. Optionally, the handle may be attachable/detachable.

Other and further aspects and embodiments will be apparent in view of the following drawings and detailed description.

BRIEF DESCRIPTION OF THE DRAWINGS

The drawings illustrate the design and utility of preferred embodiments of the inventions, in which similar elements are referred to by common reference numerals. In order to better appreciate how the above-recited and other advantages and objects of the inventions are obtained, a more particular description of the inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE ILLUSTRATED EMBODIMENTS

Figure 1:
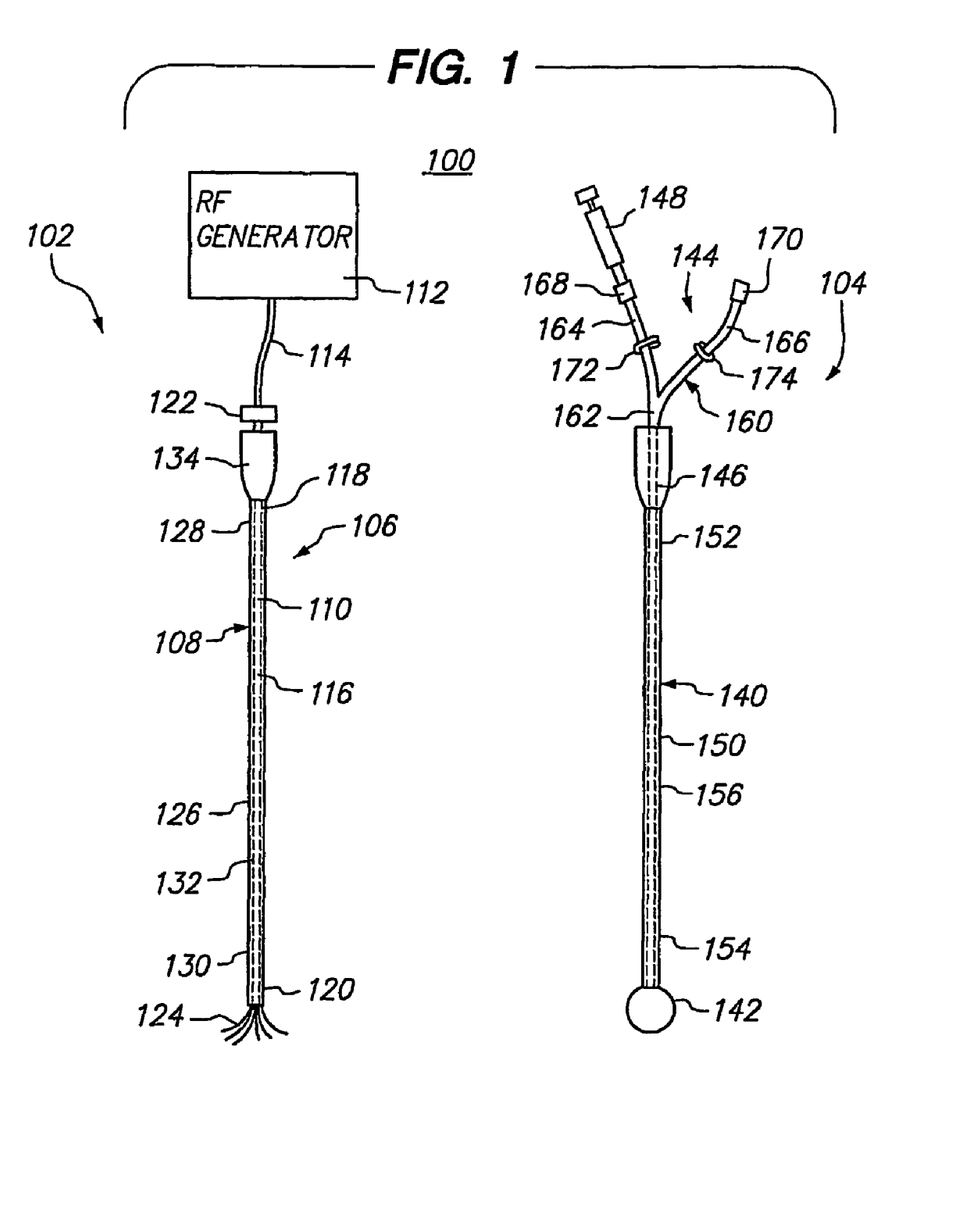
FIG. 1 is a plan view of a tissue ablation/vessel occlusion system constructed in accordance with one preferred embodiment of the inventions, wherein a tissue ablation assembly and a vessel occlusion assembly are particularly shown.

Referring to FIG. 1, a tissue ablation/vessel occlusion system 100 constructed in accordance with one preferred embodiment of the inventions is described. The ablation system 100 generally comprises a tissue ablation assembly 102 and a vessel occlusion assembly 104.

The tissue ablation assembly 102 comprises an electrosurgical probe assembly 106 that includes a cannula 108, a reciprocating RF electrosurgical probe 110 disposed within the cannula 108, and a RF generator 112 operable to deliver RF energy from the electrosurgical probe 110 (shaft portion shown in phantom) into tissue, e.g., a solid tumor within the liver of a patient. The RF generator 112 provides a standard source of RF energy for electrosurgical applications and includes a cable 114 coupled to the electrosurgical probe 110. The electrosurgical probe 110 comprises a rigid elongated shaft 116 (shown in phantom) having a proximal end 118 and a distal end 120, an electrical connector 122 mounted to the proximal end 118 of the shaft 116, and an electrode device 124 mounted to the distal end 120 of the shaft 116. The electrical connector 122 is configured to mate with the cable 114 of the RF generator 112. In the illustrated embodiment, the electrode device 124 comprises an array of tissue penetrating needle electrodes. It should be appreciated, however, that other types of electrode devices can be used.

The cannula 108 comprises an elongated rigid shaft 126 having a proximal end 128 and a distal end 130, and a lumen 132 (shown in phantom) extending through the interior of the cannula shaft 126. The cannula shaft 126 is composed of a suitable material, such as plastic, metal or the like, and has a suitable length, typically in the range from 5 cm to 30 cm, preferably from 10 cm to 20 cm. The cannula shaft 126 has an outside diameter consistent with its intended use, typically being from 1 mm to 5 mm, usually from 1.3 mm to 4 mm. The cannula shaft 126 has an inner diameter in the range from 0.7 mm to 4 mm, preferably from 1 mm to 3.5 mm.

The cannula 108 further comprises a handle 134 mounted to the proximal end 128 of the shaft 126. The shaft 116 of the electrosurgical probe 110 is reciprocally disposed within the lumen 132 of the cannula 108, so that the electrode device 124 can be alternately deployed from the distal end 130 of the cannula shaft 126 and withdrawn within the cannula shaft 126. The distal end 116 of the cannula 108 comprises a sharpened tip to allow it be percutaneously introduced through the patient's skin to deliver the distal end of the surgical probe 110 to the tissue to be treated. Further details related to the construction and operation of needle electrode array-type probe arrangements are disclosed in U.S. Pat. No. 6,379,353, entitled "Apparatus and Method for Treating Tissue with Multiple Electrodes," which is hereby expressly incorporated herein by reference.

The vessel occlusion assembly 104 is configured for being percutaneously introduced through the wall of a vessel, such as, e.g., a blood vessel, and operated to occlude the fluid flow, e.g., blood flow, through the vessel. It is designed to be operated in conjunction with the tissue ablation assembly 102 during a tissue ablation procedure, but can be operated in conjunction with other medical devices to treat tissue adjacent to the vessel. As used here, a vessel refers to any duct, canal, or other tube that contains or conveys a body fluid; thus, a vessel includes blood vessels, such as the portal vein and the hepatic artery. For brevity and clarity, the invention shall be discussed with reference to a vessel, and it should be understood to those in the art that the invention may be used in conjunction with any vessel carrying a bodily fluid within a living animal, whether human or non-human. To this end, the vessel occlusion assembly 104 generally comprises a cannula 140, an expandable/collapsible occlusive device 142, such as a balloon, a inflation medium interface 144, a handle 146, and a syringe 148.

The cannula 140 comprises a cannula shaft 150 having a proximal end 152 and a distal end 154, and a common inflation/deflation lumen 156 (shown in phantom) extending through the cannula shaft 150. The cannula shaft 150 is composed of a suitable material, such as plastic, metal or the like, and has a suitable length similar to the cannula shaft 108 of the electrosurgical probe assembly 106.

The balloon 142 is mounted to the distal end 154 of the cannula shaft 150. As used herein, a balloon 142 may include any expandable member capable of being expanded. In other words, for ease of explanation, the operation of embodiments of the invention shall be described with reference to a balloon 142, but it is contemplated that other expandable members may be used as an equivalent to the balloon 142. The balloon 142 is preferably made of a compliant material, such as, e.g., latex, Pebax®, C-flex®, urethane or silicone. Preferably, the balloon 142 has a fully inflated diameter that is consistent with the inner diameter of the vessel in which the balloon 142 to be introduced into, e.g., about one to three centimeters.

Figure 2:
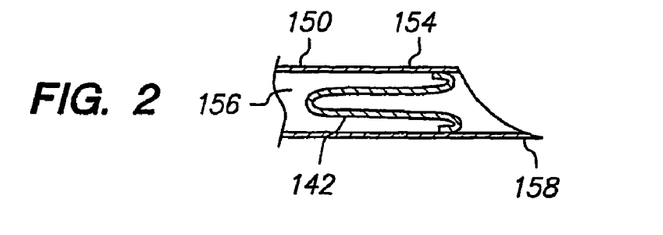
FIG. 2 is a partially cut-away cross-sectional view of the distal end of a vessel occlusion assembly of FIG. 1, wherein the balloon is particularly shown in a deflated state.
Figure 3:
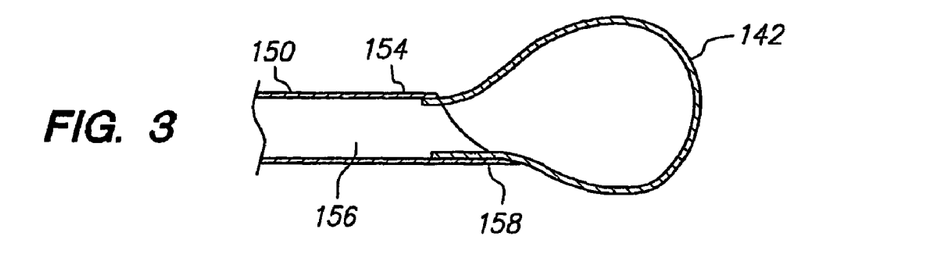
FIG. 3 is a partially cut-away cross-sectional view of the distal end of the vessel occlusion assembly of FIG. 1, wherein the balloon is particularly shown in an inflated state.

Referring now to FIG. 2 and FIG. 3, the distal end 154 of the cannula shaft 150 includes a sharpened distal tip 158 for piercing through a patient's abdomen wall, e.g., percutaneously through skin and intervening tissue into the vessel. The distal tip 158 is preferably echogenic, thereby allowing it to be seen as an acoustic shadow when ultrasonically imaged. In the illustrated embodiment, the balloon 142 is mounted proximate the distal tip 158, such that its interior is in fluid communication with the common lumen 156.

When deflated, as shown in FIG. 2, the balloon 142 is preferably carried completely inside of the distal portion of lumen 156, so as to not interfere with, or be damaged by, the sharp distal tip 158. For example, the opening of the balloon may be bonded or otherwise attached circumferentially about an interior wall of lumen 156, thereby substantially sealing the lumen 156. The balloon 142 is configured to inflate distally beyond the distal tip 158 of the cannula 140 when a medium, such as saline or contrast agent, is conveyed distally through the common lumen 156 into the interior of the balloon 142, as shown in FIG. 3, and is configured to deflate and withdraw back within the distal end of the lumen 156 when the inflation medium is conveyed from the interior of the balloon 142 proximally through the common lumen 156, shown in FIG. 2.

Alternatively, separate inflation and deflation lumens made be provided through the cannula 140, with each of the separate lumens in communication with the interior of the balloon 142. In this case, the balloon 142 is configured to inflate when the medium is conveyed distally through the separate inflation lumen, and deflate when the medium is conveyed proximally through the separate deflation lumen.

The inflation medium interface 144 comprises a flexible branched tubing assembly 160 having a common branch 162 mounted within the proximal end 152 of the cannula shaft 150 in fluid communication with the common lumen 156, and first and second branches 164 and 166 extending from the common branch 146. The tubing assembly 160 may be composed of a suitable material, such as, e.g., hypodermic polyimide catheter tubing. The medium interface 144 further comprises an inflation port 168 mounted to the proximal end of the first branch 164, and a deflation port 170 mounted to the proximal end of the second branch 166. The medium interface 144 further comprises a pair of clamps 172 and 174 disposed on the respective branches 164 and 166 for sealing the respective inflation and deflation ports 168 and 170. In the illustrated embodiment, the inflation and deflation ports 168 and 170 are configured for mating with the syringe 148. Alternatively, the inflation and deflation ports 168 and 170 can be configured for mating with a pump or some other automated device.

Thus, to inflate the balloon 142 distally beyond the distal tip 158 of the cannula shaft 150, the fluid medium is injected through the inflation port 168 with the syringe 148, while the deflation port 170 is sealed with the clamp 174, to create a positive pressure within the interior of the balloon 142. To deflate and withdraw the balloon 142 within the distal end 154 of the cannula shaft 150, the fluid medium is withdrawn from the deflation port 170 with the syringe 148, while the inflation port 168 is sealed with the clamp 172, to create a negative pressure within the interior of the balloon 142.

It should be noted that the existence of separate inflation and deflation ports 168 and 170 allows the physician to conveniently remove any air bubbles within the interior of the balloon 142 by conveying the medium, while leaving both ports 168 and 170 unclamped. In this manner, any air bubbles within the interior of the balloon 142 are flushed out through the unclamped deflation port 170 when the medium is injected into the inflation port 168. Alternatively, a single inflation/deflation port can be provided, e.g., if the existence of air bubbles within the balloon 142 is not a concern or if the air bubbles can be removed from the balloon 142 using another technique.

Figures 4, 5:
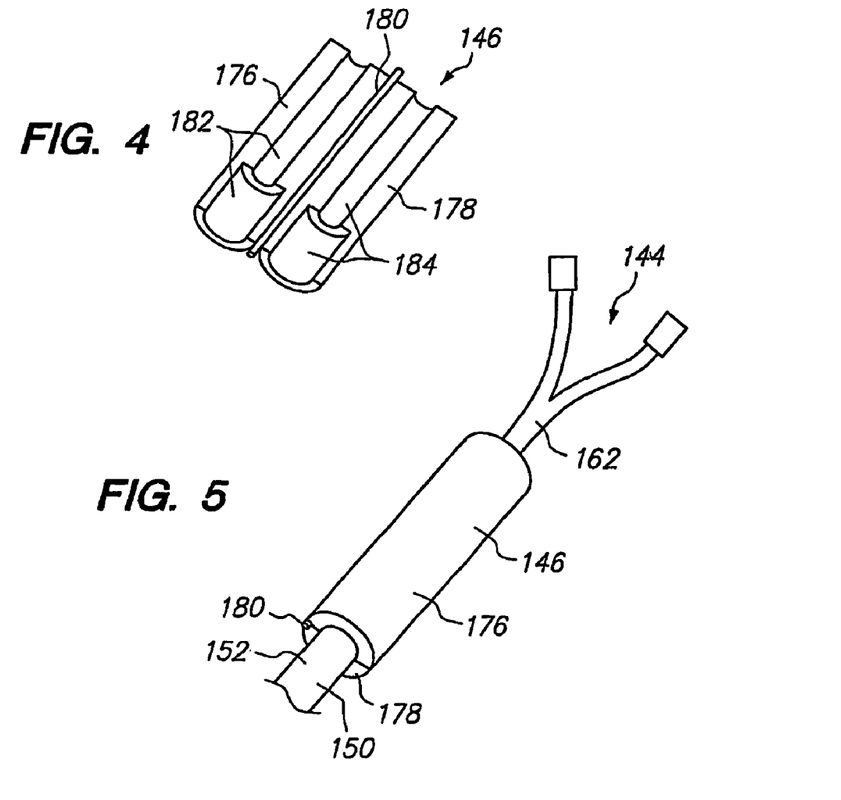
FIG. 4 is a perspective view of an attachable/detachable handle used by the vessel occlusion assembly of FIG. 1, wherein the handle is particularly shown opened.
FIG. 5 is a perspective view of the attachable/detachable handle of FIG. 4, wherein the handle is particularly clamped on the proximal end of the vessel occlusion assembly of FIG. 1.

The handle 146 provides for easy handling of the vessel occlusion assembly 104 by the surgeon or radiologist during the procedure. In the illustrated embodiment, the handle 146 is an attachable/detachable handle that can be alternately clamped around, and removed from, the proximal end 152 of the cannula shaft 150 and the common branch 162 of the tubing assembly 160 once the distal end 154 of the cannula shaft 150 is placed in the vessel to be occluded. By using an attachable-detachable handle 146, the access procedure is made easier, since the length of the cannula 140 can be reduced to only that needed to reach from the interior of the vessel to slightly outside of the abdomen wall of the patient. Employing an attachable/detachable can be helpful in a CT or MRI environment, which have working diameters that require the use of relatively short electrodes. Employing a removable handle would reduce the overall length of the device.

In the illustrated embodiment, the handle 146 comprises two clam-shell portions 176 and 178 and a hinge 180 coupling the portions 176 and 178 together. The respective handle portions 176 and 178 have respective recesses 180 and 182 formed in their facing surfaces to accommodate proximal end 152 of the cannula shaft 150 and common branch 162 of the tubing assembly 160 when the portions 176 and 178 are closed together about the hinge 180. The inflation medium interface 144 and the cannula 140 will then be affixed relative to each other to provide a fully integrated assembly. The handle portions 176 and 178 are preferably provided with some means for locking them together, e.g., an interference fit fastener (not shown) that is easily opened.

In certain embodiments, a removable handle allows the physician to remove the obstruction to the external working area, while leaving the internal occlusive device in place. This may be especially helpful if multiple occlusive devices are to be inserted in a patient as part of a single procedure. Further, if left unsupported, the weight of the handle may place a rotational force on the cannula, causing displacement of the occlusive device or other harm to the patient, especially if the occlusive device is close to the surface of the skin. The handle can be reattached as needed to facilitate removal of the occlusive device from the patient.

Figure 6:
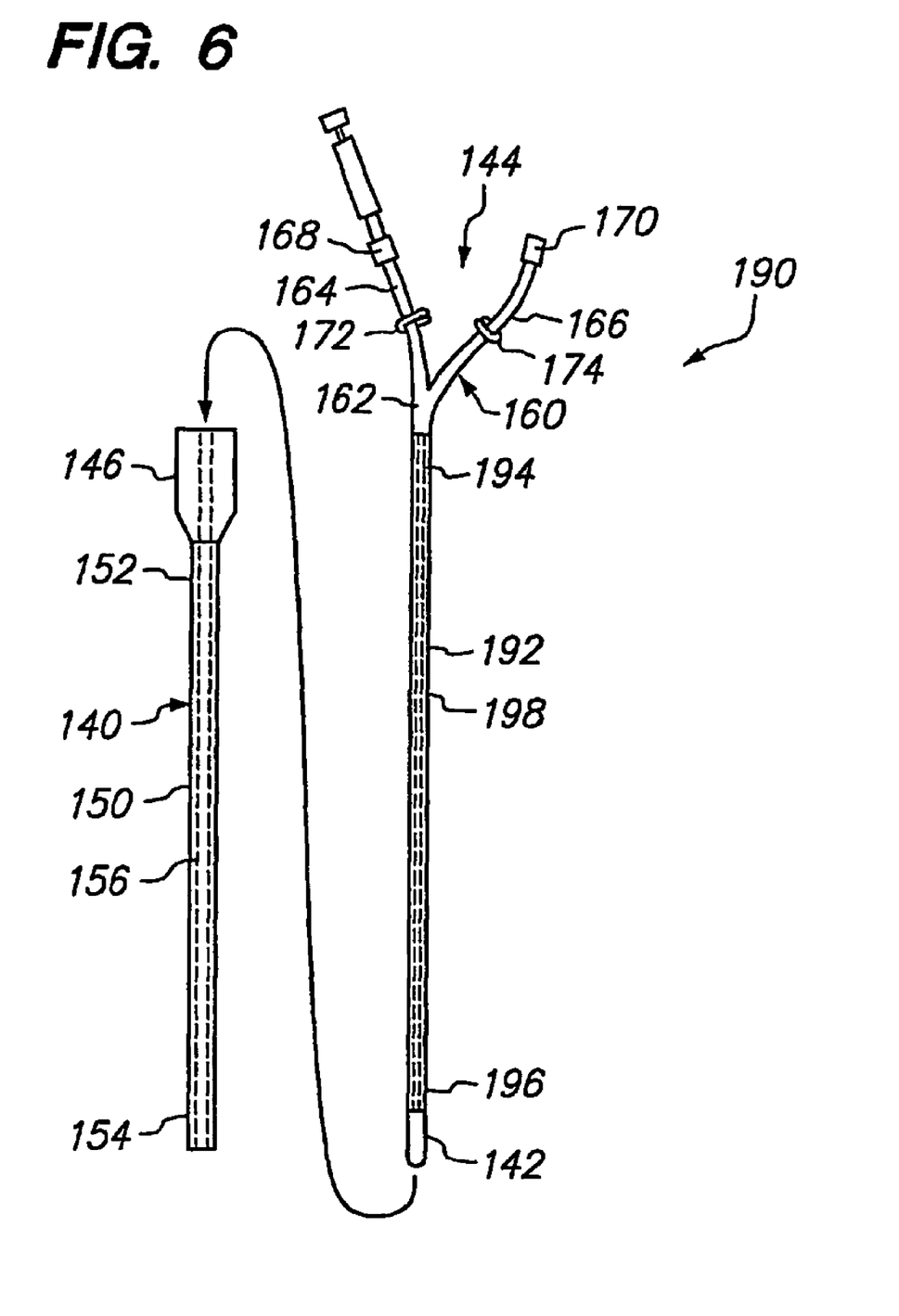
FIG. 6 is an alternative embodiment of a vessel occlusion assembly that can be used in the system of FIG. 1.

Referring now to FIG. 6, an alternative embodiment of a vessel occlusion assembly 190 that can be used with the tissue ablation/vessel occlusion system 100 is described. The vessel occlusion assembly 190 differs from the previously described vessel occlusion assembly 104 in that the balloon 142 is not mounted to the end of the cannula shaft 150. Instead, the vessel occlusion assembly 190 comprises a separate tubular member 192 that is reciprocally disposed within the lumen 156 (which acts as a device introduction lumen, rather than an inflation lumen) of the cannula 140. The tubular member 192 a proximal end 194 to which the common branch 162 of the tubing assembly 160 is mounted, a distal end 196 to which the balloon 142 is mounted, and a lumen 198 in fluid communication with the interior of the balloon 142.

The tubular member 192 may be composed of a rigid, semi-rigid, or flexible material as long as it, along with the deflated balloon 142, can be introduced through the lumen 156 of the cannula shaft 150. If composed of a flexible material, the common branch 162 of the tubing assembly 160 can actually form the tubular member 192. In the illustrated embodiment, the distal end 196 of the tubular member 192 is blunt, thereby minimizing any damage that can be caused to the balloon 142.

Thus, it can be appreciated that the balloon 142 is inflated when a medium is conveyed through the inflation port 168 from the syringe 148, through the flexible tubing assembly 160, through the lumen 198 of the tubular member 192, and into the balloon 142. The balloon 142 is deflated when the medium is conveyed from the interior of the balloon 142, out through the lumen 198 of the tubular member 192, through the flexible tubing assembly 160, and out of the deflation port 170 into the syringe 148. In one embodiment, the balloon has a flexible echogenic coating, which provides a clinical benefit in that the physician would not need to use contrast agent. Further, some contrast agents may crystallize, and clog the lumens, not allowing balloon deflation. In some embodiments, it may be desirable to coat the balloon surface with an agent to help prevent blood from clotting on the balloon surface.

Figure 7A:
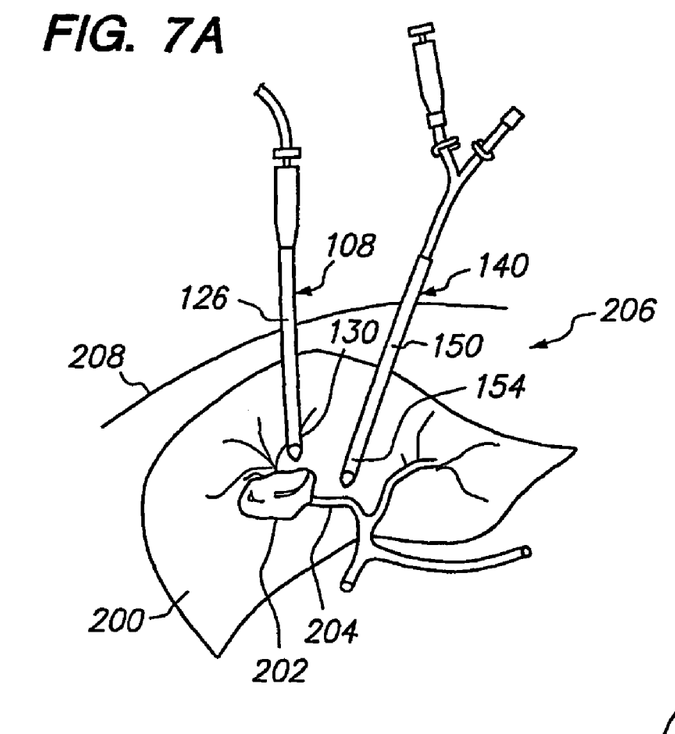
FIGS. 7A-7D illustrated perspective views of one preferred method of operating the system of FIG. 1 to ablate a tumor within the liver of a patient, while occluding the blood flow through the left hepatic artery.

Having described the structure of the tissue ablation/vessel occlusion system 100, its operation will now be described in treating a tumor 202 located in a patient's liver 204, as illustrated in FIGS. 7A-E. Initially, a doctor, e.g., a surgeon or radiologist, identifies and/or locates the patient's tumor 202 and the vessel 204 for occlusion, in this case, the portal vein, at a location upstream from the tumor 202, e.g., using ultrasound or a fluoroscope. The cannulae 108 and 140 of the respective tissue ablation assembly 102 and vessel occlusion assembly 104 are introduced into the patient's abdominal cavity 206 by piercing their distal tips through the patient's abdominal wall 208 until the distal end 130 of the cannula shaft 126 resides adjacent the tumor 202 to be treated, and the distal end 154 of the cannula shaft 150 resides adjacent the left hepatic artery 204 (FIG. 7A). It should be noted that the cannulae 108 and 140 can be introduced into the abdominal cavity 206 in any order. It should also be noted that if the non-integrated vessel occlusion assembly 190 is used rather than the vessel occlusion assembly 104, the cannula 140 can be introduced into the abdominal cavity 206 with or without the tubular member 192 and balloon 142.

The abdominal cavity 206 is preferably imaged, e.g., using ultrasound or a fluoroscope, to guide the distal ends 130 and 154 of the respective cannula shafts 126 and 150 to their desired locations. Other types of imaging modalities may be used for assisting the guiding of the cannula shafts 126 and 150 into their desired positions. For example, the cannulae 108 and 140 can be equipped with an optical viewing port for providing a distal facing view illuminated by a light source, such as a laser provided through an optical fiber.

Figure 7B:
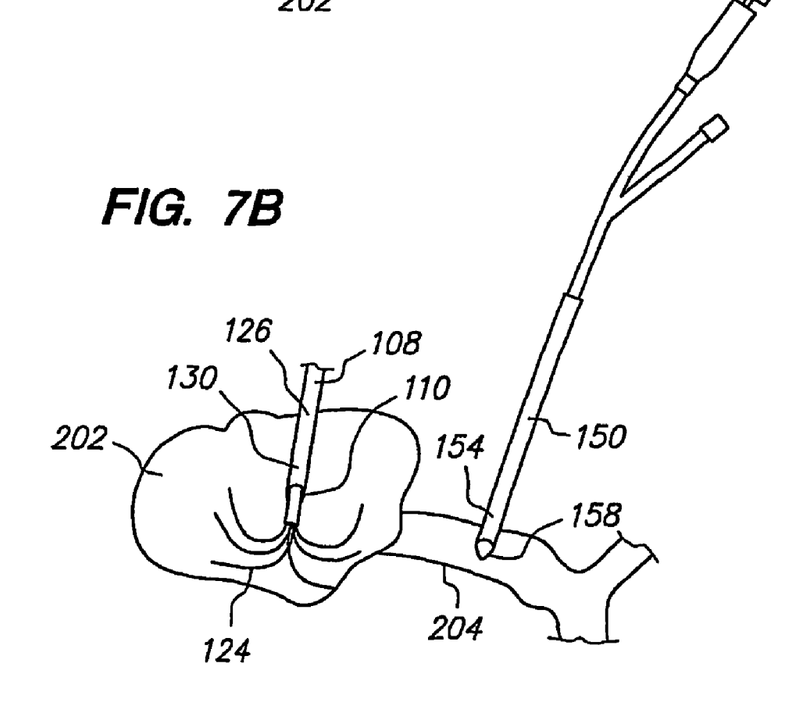
Figure 7C:
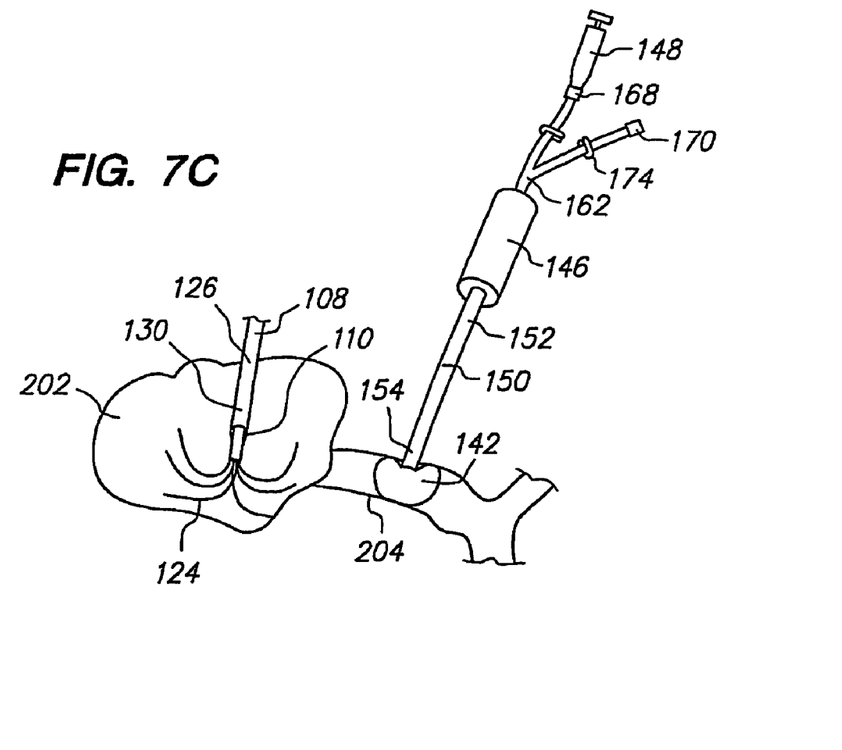

Next, the electrosurgical probe 110 is then distally pushed through the cannula 108 until the electrode device 124 is fully deployed out from the distal end 130 of the cannula shaft 126 into the tumor 202, and the distal tip 158 of the cannula shaft 150 is pierced through the wall of the vessel 204, such that it resides within the lumen of the vessel 204 (FIG. 7B). Again, this can be accomplished in any order. Next, the handle 146 is clamped onto the proximal end 152 of the cannula shaft 150 and the common branch 162 of the tube assembly 160, and then the balloon 142 is inflated out from the distal end 154 of the cannula 140 into the lumen of the vessel 204 by injecting the medium from the syringe 148 through the inflation port 168, while the deflation port 170 is clamped off with clamp 174 (FIG. 7C). As a result, the blood flow through the blood vessel 204 is occluded, thereby cutting off any blood flow to the tumor 202. If the non-integrated vessel occlusion assembly 104 is utilized, the tubular member 192 and balloon 142 are preferably disposed within the lumen 156 of the cannula 140, so that blood does not flow back through the cannula 140.

Figure 7D:
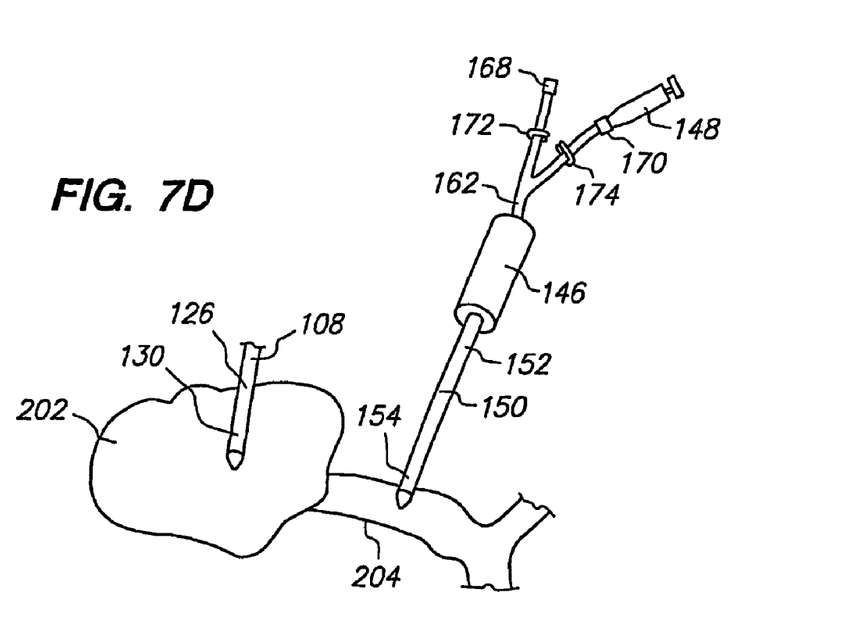

The RF generator 112 is then operated to convey RF energy from the electrode device 124 into the tumor 202, thereby ablating at least a portion of the tumor 202. Depending on the size of the tumor 202, the ablation process can be repeated to ablate any remaining portions of the tumor 202. After the ablation process is completed, the electrode device 124 is withdrawn into the distal end 130 of the cannula shaft 130 by proximally pulling the electrosurgical probe 110, and the balloon 142 is deflated and withdrawn into the distal end 145 of the cannula shaft 145 by withdrawing the medium from the deflation port 170 into the syringe 148, while the inflation port 168 is clamped off with the clamp 172 (FIG. 7D). Alternatively, the balloon 142 can be deflated between ablation steps to intermittently supply blood flow to the liver should it become necessary. The cannulae 108 and 140 are then removed from the patient's abdominal cavity 206.

Although particular embodiments of the inventions have been shown and described, it will be understood that there is no intention to limit the inventions to the illustrated preferred embodiments, and it will be obvious to those skilled in the art that various changes and modifications may be made without departing from the scope of the following claims and their equivalents.

By way of non-limiting examples, it may be desirable to use more than one occlusion device in a patient for a single procedure. In may also be desirable to use the cannula or other delivery device for inserting objects other than the occlusion balloon, such as temperature sensors or therapeutic agents. It may be desirable to shape the occlusion balloon so that it fills a particular vessel shape that is not round. It may be desirable to add one or more fluid lumens through the insertion cannula that are in communication with respective distal ports external to the balloon, e.g., for injecting a dye into, or for aspiration of, the occluded vessel or ablation site. In alternate embodiments, a hydrogel passed through a lumen may be used in place of the balloon as the occlusive member.

By way of further non-limiting examples, the occlusion device may be inserted into the vessel site through a small needle, where upon the needle is removed, leaving the balloon in place in the vessel, with an inflation lumen extending out of the patient. The occlusion balloon may alternatively be placed with a traditional introducer, such as used in a Seldinger technique for accessing blood vessels.

What is claimed is:

1. A tissue ablation system, comprising:
   an ablation probe, including:
      a rigid elongated ablation member having a tissue piercing distal end; and
      a tissue ablative element carried by the distal end of the ablation member;
   a vessel occlusion probe, including:
      a rigid elongated occlusion member having a lumen and a tissue piercing distal end; and
      an expandable occlusive device attached circumferentially to an interior wall of the occlusion member lumen, the expandable occlusive device configured for being expanded distally beyond the tissue piercing distal end of the occlusion member to at least partially occlude fluid flow through a vessel lumen when the distal end of the occlusion member is disposed within the vessel lumen.

2. The tissue ablation system of claim 1, wherein the occlusive device is an expandable/collapsible occlusive device configured to be collapsed, such that the fluid flow through the vessel lumen is unobstructed.

3. The tissue ablation system of claim 1, wherein the occlusive device is configured to be expanded to completely occlude the fluid flow through the vessel lumen.

4. The tissue ablation system of claim 1, wherein the occlusive device, when expanded, has a diameter within the range of 1-3 centimeters.

5. The tissue ablation system of claim 1, wherein the occlusive device, when expanded, has a profile that is substantially greater than a profile of the occlusion member.

6. The tissue ablation system of claim 1, wherein the vessel is one of a hepatic artery or a portal vein.

7. The tissue ablation system of claim 1, wherein the occlusive device comprises a balloon configured to be expanded when a medium is introduced into the balloon.

8. The tissue ablation system of claim 1, further comprising an actuator configured for expanding the occlusive device.

9. The tissue ablation system of claim 8, wherein the occlusive device comprises an expandable balloon, and the actuator comprises a syringe in fluid communication with the balloon.

10. The tissue ablation system of claim 1, wherein the tissue ablative element comprises an electrode.

11. The tissue ablation system of claim 1, wherein the tissue ablative element comprises an array of deployable needle electrodes.

12. The tissue ablation system of claim 1, wherein the ablation member includes a cannula having a lumen and a reciprocating shaft slidably disposed within the cannula lumen.

13. The tissue ablation system of claim 1, further comprising an ablation source operably coupled to the tissue ablative element.

14. The tissue ablation system of claim 1, wherein the occlusive device comprises a balloon, and wherein an interior of the balloon is in communication with the lumen of the occlusion member.

15. The tissue ablation system of claim 1, wherein the occlusive device, when collapsed, is configured for being disposed completely inside of the lumen of the occlusion member.

* * * * *